United States Patent [19]

Rosenbaum et al.

[11] Patent Number: 5,709,878
[45] Date of Patent: Jan. 20, 1998

[54] TRANSDERMAL DELIVERY OF DEHYDROEPIANDROSTERONE

[76] Inventors: Jerry Rosenbaum, 5901 SW. 94 St., Miami, Fla. 33156; George Suarez, 741 N. Green Way, Coral Gables, Fla. 33143

[21] Appl. No.: 691,244

[22] Filed: Aug. 2, 1996

[51] Int. Cl.$^6$ .................................................. A61F 13/00
[52] U.S. Cl. .................. 424/449; 424/447; 514/944; 514/969
[58] Field of Search .................. 424/449, 447; 514/944, 969

[56] References Cited

U.S. PATENT DOCUMENTS

| | | | |
|---|---|---|---|
| 4,340,594 | 7/1982 | Mizushima | 424/238 |
| 4,780,455 | 10/1988 | Lieberman | 514/77 |
| 4,783,450 | 11/1988 | Fawzi et al. | 514/78 |
| 4,892,737 | 1/1990 | Bodor et al. | 424/449 |
| 4,906,463 | 3/1990 | Cleary et al. | 424/78 |
| 4,978,532 | 12/1990 | El-Rashidy | 424/448 |
| 5,008,111 | 4/1991 | Bodor | 424/449 |
| 5,075,113 | 12/1991 | DuBois | 424/450 |
| 5,204,119 | 4/1993 | Shiobar et al. | 424/489 |
| 5,206,008 | 4/1993 | Loria | 424/45 |
| 5,231,090 | 7/1993 | Hsia et al. | 514/78 |
| 5,314,906 | 5/1994 | Bombardelli | 514/411 |
| 5,332,576 | 7/1994 | Mantelle | 424/443 |
| 5,484,833 | 1/1996 | Bombardelli | 424/449 |
| 5,518,730 | 5/1996 | Fuisz | 424/426 |

FOREIGN PATENT DOCUMENTS 9321970   11/1993   WIPO.

*Primary Examiner*—D. Gabrielle Phelan
*Attorney, Agent, or Firm*—Robert M. Schwartz

[57] ABSTRACT

Disclosed is a novel transdermal delivery system for dehydroepiandrosterone (DHEA). Using phospholipids as vehicles, DHEA can be administered into and through the skin when topically applied. Numerous advantages apply to this modality of therapy.

16 Claims, No Drawings

TRANSDERMAL DELIVERY OF DEHYDROEPIANDROSTERONE

BACKGROUND OF THE INVENTION

1. Field of the Invention

This invention relates to the adrenal hormone dehydroepiandrosterone (DHEA, Chemical Abstracts registry number 53-43-0, systematic name 3-beta-hydroxyandrost-en-17-one) and to improved compositions and methods for topical administration thereof.

DHEA is the major secretory product of the human adrenal gland and is the most abundant hormone in the body. It is weakly active as a sex hormone but is a precursor within the body for the androgen testosterone in the male and for estrogenic hormones such as estrone and estradiol in the female. Once DHEA is released into the body from the adrenal gland it is converted into the sulfate ester DHEA-S by the liver.

The liver and the kidney are the principal organs involved in clearing steroid hormones from the circulation. Hepatic metabolism accomplishes two functions for DHEA: a decrease in the biologic activity of the hormone, and an increase in its water solubility, because of conversion to the hydrophilic sulfate form that can be excreted in urine.

Amounts of DHEA in the circulation change with age (Table 1) and it has therefore been postulated that they may be involved in the maturing and aging process in humans.

TABLE 1

REFERENCE RANGES OF DEHYDROEPIANDROSTERONE SULFATE

| Age (years) | Males, micrograms/ml | Females, micrograms/ml |
|---|---|---|
| Newborn | 1.7–3.6 | 1.7–3.6 |
| Prepubertal | 0.1–0.6 | 0.1–0.6 |
| Postpubertal–29 | 1.4–7.9 | 0.7–4.5 |
| 30–39 | 1.0–7.0 | 0.5–4.1 |
| 40–49 | 0.9–5.7 | 0.4–3.5 |
| 50–59 | 0.6–4.1 | 0.3–2.7 |
| 60–69 | 0.4–3.2 | 0.2–1.8 |
| 70–79 | 0.3–2.6 | 0.1–0.9 |

Source: Smith Kline Beecham Clinical Laboratories Co.

Blood levels of DHEA-S peak at approximately 20 years of age and then decline past that age in many individuals. Clinical studies have shown a correlation between a decrease in DHEA-S and an increase in age related conditions.

The plasma half-life of free DHEA is under twenty minutes. In its bound form as DHEA-S it dissociates more rapidly from the binding proteins, making them more susceptible to degradation. The episodic secretion of DHEA, combined with this short plasma half-life results in wide fluctuations in plasma free DHEA levels. By contrast, the steroid sulfates (with significantly less biological activity), such as DHEA-S, which bind with high affinity to albumin, are cleared slowly from the circulation and have high stable plasma concentration.

2. Prior Art

El-Rashidy U.S. Pat. No. 4,978,532 discloses a transdermal dosage form for administering dehydroepiandrosterone (DHEA), utilizing a pressure-sensitive medical grade silicone adhesive material which contains DHEA and a permeation enhancer therefor. A "permeation enhancer" is defined as a compound compatible with DHEA that facilitates the uptake of DHEA through the skin and thus enables a therapeutically effective dosage of DHEA to be administered to the patient. The permeation enhancers contemplated are aromatic or aliphatic carbocyclic compounds that have pendant hydroxyl groups, such as butylated hydroxytoluene (BHT), butylated hydroxyanisole (BHA), a hydroxypropyl-beta-cyclodextrin (HPBCD), and the like, as well as mixtures thereof.

El-Rashidy states that "DHEA in the presently contemplated dosage forms can be administered to lower elevated blood cholesterol levels, for prophylactic or palliative treatment of patients suffering from AIDS, heart disease, obesity, diabetes, and the like afflictions." However, no results of such administration to patients are disclosed.

Loria U.S. Pat. No. 5,206,008 cites such clinical uses of DHEA as topical treatment of patients suffering from psoriasis, gout, and hyperlipemia, and administration to postcoronary patients. Loria further discloses the conversion of DHEA, both in the body and by chemical synthesis, to 5-androstene-3-beta-17-beta-diol and 5-androstene-3-beta-7-beta-17-beta-triol, and teaches the clinical use of these two metabolites in preference to DHEA.

Fawzi et al U.S. Pat. No. 4,783,450 discloses that lecithin enhances the penetration of a drug through the skin as well as a pharmaceutical composition adapted for transdermal administration comprising an active ingredient and an effective amount of lecithin. An active ingredient is defined as "an effective amount of any therapeutically active drug". The "preferred drugs" recited by categories and specific compounds do not include DHEA or any steroid or any kind of hormone.

Hsia et al U.S. Pat. No. 5,231,090 discloses a method of lowering serum cholesterol levels in mammals comprising topically administering a phospholipid containing composition such as lecithin with a pharmaceutically acceptable carrier, which can be "any carrier that does not affect the affinity of the phospholipid for cholesterol". The phospholipid containing composition can be present, for example, in a patch which can be adhered to the skin of the individual such that topical administration is effected. There is no mention of any clinically active material to be used together with lecithin. Hence there is no teaching that a phospholipid is of any benefit in increasing serum levels of any substance.

DuBois U.S. Pat. No. 5,075,113 discloses dietetic, laxative, or cosmetic products which are emulsions of an aqueous phase in an oily phase, in which the aqueous phase contains an extract of hydrodispersible lecithin enriched in phosphatidylcholine, and the oily phase is composed principally of oily paraffin hydrocarbons and a purified liposoluble lecithin extract. The products can contain an inert mineral powder such as kaolin, talc or calcium carbonate, and monoglycerides melting above 50° C., as well as a variety of flavors. There is no mention or suggestion of transdermal administration of any therapeutic by using the disclosed composition.

Against this background there remains a need for improved methods and compositions for topically administering DHEA and achieving novel therapeutic utilities thereof.

SUMMARY OF THE INVENTION

In accordance with this invention, a non-staining topical composition for enhancing the serum concentration of dehydroepiandrosterone in a mammal being topically administered said composition, comprises an effective amount of at least one dehydroepiandrosterone compound and an amount effective to increase the transdermal transmission thereof of at least one phospholipid.

The term "non-staining" is used to express the substantial absence of color formation on the skin or clothing of one to whom the composition is topically administered, alone or in the presence of one or more agents such as heat, sunlight, artificial light sources, mild to moderate acid solutions having a pH greater than 2 and less than 7, or mild to moderate alkaline solutions having a pH greater than 7 to 12.

In a human subject, an increase in the serum concentration of dehydroepiandrosterone, including free DHEA as well as the sulfate conjugate DHEA-S, over the baseline level can be noted within a day of topical administration of the composition. On continued administration, the serum concentration of dehydroepiandrosterone continues to rise until a peak level at least double the base line concentration and approaching the peak concentration observed in young adults is reached in fourteen days or less, and is maintained at or close to the peak level as long as topical administration of the composition is continued. Consequently, prolonged or even indefinite topical administration of the composition of the invention is safe.

Topical administration of the composition of this invention can provide a number of therapeutic benefits to the recipient thereof in improving all conditions that benefit from treatment with dehydroepiandrosterone. Such benefits include without limitation weight loss, reduction of cellulite, reduction of wrinkles, reduction of malignancy, increased skin elasticity, increased libido in men and women, diminished male erectile dysfunction, improvements in such conditions as systemic lupus erythematosus and seripositive rheumatoid arthritis, hair growth, enhanced memory capability, reduced levels of low density lipoprotein cholesterol, and improvements in general perception of well-being and energy.

The quantities of the composition of this invention that need to be administered in order to achieve the increased serum concentrations of dehydroepiandrosterone and provide the therapeutic benefits are modest, particularly when compared to oral doses given in attempting to achieve the same results.

DESCRIPTION OF PREFERRED EMBODIMENTS

Dehydroepiandrosterone compounds that can be used in the composition of this invention include dehydroepiandrosterone itself, dehydroepiandrosterone sulfate, and fluorinated derivatives of dehydroepiandrosterone such as 16-fluorodehydroepiandrosterone (CAS registry no. 1649-27-0, systematic name 3-beta-hydroxy-16-fluoroandrost-5-en-17-one). Dehydroepiandrosterone of sufficient purity for use in the composition of this invention is commercially available. Mixtures of more than one dehydroepiandrosterone compound can be used.

Phospholipids that can be used in the composition of this invention include phosphatidylcholine, phosphatidylethanolamine, and phosphatidylserine and mixtures thereof. The fatty acid groups in the phosphatidyl moieties of these phospholipids can be saturated, monounsaturated or polyunsaturated groups such as lauroyl, linoleyl, myristoyl, oleoyl, palmitoyl, and stearoyl groups. Soy lecithin, a mixture of phospholipids rich in monounsaturated and polyunsaturated phosphatidylcholines is particularly preferred.

In the composition of the invention, the concentration of dehydroepiandrosterone compound is in the range of 0.1 to 25 grams per 100 grams of composition, preferably 0.2 to 15 grams per 100 grams, and the concentration of phospholipid is in the range of 1 to 90 grams per 100 grams of composition, preferably 2 to 75 grams per 100 milliliters. The relative proportions of phospholipid to dehydroepiandrosterone compound preferably range from 1:1 to 300:1, most preferably from 2:1 to 250:1.

Dehydroepiandrosterone and phospholipid can be combined with little or no other material present into a concentrate suitable for facilitating the subsequent compounding of a variety of formulations presenting the composition of this invention. Surprisingly, even greater concentrations of dehydroepiandrosterone can be achieved in a mixed solvent system combining phospholipid with ethyl alcohol, cetyl alcohol, and a medium chain length triglyceride. Such concentrates can conveniently include 10 to 15 parts by weight of dehydroepiandrosterone and 85 to 90 parts of phospholipid.

Presentations for use of the composition of this invention can, for example, take the form of pastes, gels, and liquids such as solutions, emulsions, creams, and lotions.

In addition to dehydroepiandrosterone compound and phospholipid, the composition of the invention can include a topically acceptable carrier and such adjuvants as are helpful for convenient dispensing and application of the composition by such presentations as pastes, gels, liquid forms such as solutions, emulsions, creams, and lotions, as well as transdermal delivery systems.

Pastes are liquids whose viscosity is enhanced to the point that flow is largely inhibited by the presence of undissolved as well as dissolved solids which can be waxes or finely divided inorganic solids.

Gels are semisolid systems of either containing suspended small inorganic particles (two phase gels) or organic macromolecules interpenetrated by a liquid (single phase gels).

Solutions are single phase liquids substantially free of solid but small amounts of haze or cloudiness can be tolerated.

Emulsions, lotions, and creams are multiphase liquids containing special components known as surfactants that inhibit or delay the separation of the phases. In the composition of this invention, the phospholipid component can function as surfactant. Added surfactants are therefore not necessary but can be included if desired.

Suitable carriers and adjuvants are selected with a view to being safe in prolonged or even indefinite application of the composition, and include:

Solvents such as ethanol, ethyl acetate, glycerine, polyethylene glycols with average molecular weight ranging from 200 to about 1100, and propylene glycol (water miscible); heptane, purified isoparaffinic hydrocarbons boiling in the range from 60° to 300° C. and fractions thereof, canola oil, olive oil, and mineral oil (not miscible with water);

Emollients such as petrolatum, paraffin wax, beeswax, cetyl palmitate, and lanolin;

Emulsifiers and surfactants such as sodium, potassium, and triethanolamine salts of oleic and stearic acids (which can be prepared in situ by including in the formulation suitable sodium, potassium and amine bases along with the desired acids), dioctyl sodium sulfosuccinate, sodium dodecyl sulfate, glycerol monooleate, glycerol monostearate, and ethoxylated sorbitan esters such as Polysorbate 20, Polysorbate 65 and Polysorbate 80;

Finely divided solids such as aluminum hydroxide, bentonite, kaolin, magnesium silicate, silica, titanium dioxide, and zinc oxide;

Thickeners such as agar, carrageenan, food starch, modified starch, gelatin, gum arabic, guar gum, hydroxyethylcellulose, hydroxypropyl methylcellulose, pectin, sodium carboxymethylcellulose and polyacrylic acid adjusted in pH to provide the desired extent of thickening;

Antioxidants and preservatives such as benzalkonium chloride, di-coco-dimethylammonium chloride, dilauryl thiodipropionate, methyl parahydroxybenzoate, propyl parahydroxybenzoate, and tocopherol.

Particularly preferred carriers and adjuvants include medium chain length triglycerides having six to ten carbon atoms in each fatty acid chain, straight chain aliphatic alcohols having twelve to twenty carbon atoms, ethanol, and water. Examples of suitable medium chain length triglycerides include tricaprylin, tricaprin, and a high purity mixed C8–C10 triglyceride available from Unilever GmbH of Hamburg, Germany, under the trade name HB-307. Examples of suitable straight chain aliphatic alcohols include behenyl alcohol, cetyl alcohol, lauryl alcohol, myristyl alcohol, oleyl alcohol, stearyl alcohol and mixtures thereof.

When formulated for presentation as a solution, the composition of the invention can include volatile carriers such as ethanol and water as well as non-volatile carriers such as medium chain length triglyceride and straight chain aliphatic alcohols having twelve to twenty carbona toms to supplement or substitute for volatile carriers. Thus a typical solution composition of the invention includes a concentration of dehydroepiandrosterone compound in the range of 0.5 to 15 grams per 100 grams of composition, preferably 2 to 15 grams per 100 grams, a concentration of phospholipid in the range of 5 to 75 grams per 100 grams of composition, preferably 10 to 65 grams per 100 grams, a concentration of volatile carrier in the range of 0 to 90 grams per 100 grams, and a concentration of non-volatile carrier in the range of 0 to 30 grams per 100 grams.

When formulated for presentation as a lotion, the composition of the invention can, if desired, include a finely divided solid and a thickener. Thus a typical lotion composition of the invention includes a concentration of dehydroepiandrosterone compound in the range of 0.2 to 10 grams per 100 grams of composition, preferably 1 to 5 grams per 100 grams, a concentration of phospholipid in the range of 2 to 30 grams per 100 grams of composition, preferably 4 to 25 grams per 100 grams, a concentration of finely divided solid in the range of 0 to 5 grams per 100 grams of composition and a concentration of thickener in the range of 0 to 5 grams per 100 grams of composition.

When formulated for presentation as a cream, the composition of the invention can, if desired, include an emollient and an emulsifier, as well as an antioxidant and/or preservative. Thus a typical cream composition of the invention includes a concentration of dehydroepiandrosterone compound in the range of 0.1 to 10 grams per 100 grams of composition, preferably 0.25 to 5 grams per 100 grams; a concentration of phospholipid in the range of 2 to 75 grams per 100 grams of composition, preferably 3 to 65 grams per 100 grams; a concentration of emollient in the range of 0 to 50 per 100 grams of composition and a concentration of emulsifier in the range of 0 to 25 grams per 100 milliliters of composition.

When formulated for presentation as a paste, the composition of the invention can, if desired, include a thickener and/or finely divided solid in greater concentrations than in a lotion. Thus a typical paste composition of the invention includes a concentration of dehydroepiandrosterone compound in the range of 1 to 10 grams per 100 grams of composition, preferably 2 to 5 grams per 100 grams; a concentration of phospholipid in the range of 2 to 50 grams per 100 grams of composition, preferably 5 to 40 grams per 100 grams; a concentration of finely divided solid in the range of 0 to 15 grams per 100 grams of composition, and a concentration of thickener in the range of 0 to 15 grams per 100 grams of composition, the combined concentration of finely divided solid and thickener being at least 5 grams per 100 grams of composition.

When formulated for presentation as a gel, the composition of the invention can include a gelling agent such as a finely divided solid and/or a thickener in concentrations that produce a loose molecular network inhibiting the free movement of liquid ingredients. Thus a typical gel composition of the invention includes a concentration of dehydroepiandrosterone compound in the range of 0.1 to 10 grams per 100 grams of composition, preferably 0.25 to 5 grams per 100 grams; a concentration of phospholipid in the range of 2 to 50 grams per 100 grams of composition, preferably 3 to 25 grams per 100 milliliters; a concentration of finely divided solid in the range of 0 to 15 grams per 100 grams of composition, and a concentration of thickener in the range of 0 to 15 grams per 100 grams of composition, the combined concentration of finely divided solid and thickener being at least 1 gram per 100 grams of composition.

In a particularly preferred embodiment, the composition of this invention is administered to the recipient by means of a transdermal delivery system or patch. Transdermal delivery is accomplished by exposing a source of the substance to be administered to the recipient's skin for an extended period of time. Typically, the substance is incorporated in a matrix or container from which it is released onto the recipient's skin. The rate of release can be controlled by a membrane placed between the container and the skin, by diffusion directly from the container, or by the skin itself serving as a rate-controlling barrier. Many suitable transdermal delivery systems and containers therefor are known, ranging in complexity from a simple gauze pad impregnated with the substance to be administered and secured to the skin with an adhesive bandage to multilayer and multicomponent structures. All such systems are characterized by the use with the substance to be administered of a shaped article sufficiently flexible to snugly fit to the skin of the recipient and thus serve both as container from which the substance is delivered to the recipient's skin and as barrier to prevent loss or leakage of the substance away from the area of the skin to which the substance is to be delivered. For brevity, such a flexible article is referred to in the instant specification and claims as a reservoir.

Typically, a transdermal delivery system or patch also contains an added substance that assists the penetration of the active ingredient through the skin, usually termed a skin enhancer or penetration enhancer. Many penetration enhancers are known in the art, both water soluble and water insoluble. It has been discovered in accordance with this invention that the phospholipid component of the composition of this invention is outstandingly effective in assisting the penetration of a dehydroepiandrosterone compound through the skin and the establishment of increased serum concentrations of dehydroepiandrosterone sulfate in the recipient.

Accordingly, a transdermal delivery system according to this invention comprises a reservoir, a dehydroepiandrosterone compound as the active ingredient, and a phospholipid compound as penetration enhancer in sufficient concentration to effect increased serum concentration of dehydroepiandrosterone in the recipient. Conventional penetration enhancers are not necessary but can be included if desired.

Compositions according to this invention can be prepared by conventional procedures. To minimize contamination from the growth of microorganisms, sterilized equipment is preferably used. Once blended, the composition can be packaged and stored in any suitable container inert to the contents including aluminum, glass, stainless steel, and solvent resistant plastics including polyamide, polyester, polypropylene, and ABS polymer. Storage is preferably in a cool place away from strong light. Continued sterility can be assured by conventional techniques including aseptic packaging and post-sterilization in the final package by electron beam exposure.

In use, compositions according to this invention are applied to areas of the skin of the recipient in any suitable manner. Thus, a solution or emulsion of the composition can be brushed or painted on desired areas of the recipient's body. A paste, gel, cream, or lotion can be taken on the palm of the hand and rubbed into the recipient's shoulder area, chest, abdominal area, buttocks, or thighs. Transdermal patches can be applied to the upper arm or any suitable less visible area.

Delivery of dehydroepiandrosterone to the recipient's blood stream can be confirmed by analysis of a blood sample taken from the recipient. Increased serum levels of dehydroepiandrosterone sulfate are noted within twenty-four hours and continue to increase to a plateau of at least twice baseline levels and beneficial effects thereof are noted within two weeks.

EXAMPLE 1

Preparation of a Stable Concentrated Composition of Dehydroepiandrosterone and Phospholipid A borosilicate glass flask fitted with stirrer and thermometer was mounted in a water bath heated on an electric hot plate, and charged with 45 grams of phosphatidylcholine and 19 grams of pharmaceutical grade ethyl alcohol. Heat was applied to the water bath, and stirring started as the phosphatidylcholine began to melt. When the material had melted at about 95° F., 18 grams of dehydroepiandrosterone was added in small portions over a thirty minute period, and heating at 95° F. was continued until a homogeneous melt was obtained. Heating was discontinued; 5 grams of mixed C8–C10 triglyceride, 3 grams of cetyl alcohol, and an additional 30 grams of phosphatidylcholine was added with continued stirring until the mixture had cooled to ambient temperature and could be transferred to a brown glass storage bottle.

The result of this preparation was a pale yellow liquid composition according to this invention containing 15% by weight of dehydroepiandrosterone and approximately 62.5% of phosphatidylcholine, 16% of ethanol, 4% of mixed C8–C10 triglyceride, and 2.5% of cetyl alcohol.

The composition remained liquid upon storage at ambient as well as refrigerated temperatures.

Addition of water to this product in a high speed mixture produced a cream in accordance with this invention.

EXAMPLE 2

Preparation of a Stable Concentrated Composition of Dehydroepiandrosterone and Phospholipid A borosilicate glass flask fitted with stirrer and thermometer was mounted in a water bath heated on an electric hot plate, and charged with 45 grams of phosphatidylcholine. Heat was applied to the water bath, and stirring started as the phosphatidiylcholine began to melt. When the material had melted at about 135° F., 10 grams of dehydroepiandrosterone was added in small portions over a thirty minute period, and heating at 135° F. was continued until a homogeneous melt was obtained. Heating was discontinued, and an additional 45 grams of phosphatidylcholine was added with continued stirring until the mixture was uniform and could be discharged, cooled to ambient, and broken up for storage.

The result of this preparation was a pale yellow brittle solid composition according to this invention containing 10% by weight of dehydroepiandrosterone and approximately 90% of phosphatidylcholine.

EXAMPLE 3

Preparation of an Emulsion Containing Dehydroepiandrosterone and Phosphatidylcholine A mixture of 23 grams cetyl alcohol and 24 grams petrolatum is warmed to 75° C. to give a clear melt, to which are added 1 gram of dehydroepiandrosterone and 2 grams phosphatidylcholine. Separately, 1 gram sodium lauryl sulfate, 12 grams propylene glycol, 25 milligrams of methyl p-hydroxybenzoate and 15 milligrams of propyl p-hydroxybenzoate are dissolved in 37 grams of warm water, heated to 75° C., and stirred into the melted first mixture. Stirring is continued with cooling until the resulting oil-in-water emulsion sets into a washable ointment containing approximately 1000 milligrams of dehydroepiandrosterone per 100 ml and 2000 milligrams of phosphatidylcholine per 100 ml in accordance with this invention.

EXAMPLES 4–8

Preparation of Creams Containing Dehydroepiandrosterone and Phosphatidylcholine

Creams are prepared by stirring together at 70° C. separately prepared premixes of the water-soluble ingredients and the water-insoluble ingredients tabulated below (all quantities in grams except as noted), and continuing agitation while cooling to ambient.

| Example | 4 | 5 | 6 | 7 | 8 |
|---|---|---|---|---|---|
| water-insoluble: | | | | | |
| cetyl palmitate | 23 | — | — | — | — |
| beeswax | 23 | — | 10 | — | — |
| mineral oil | 105 | — | 30 | — | — |
| petrolatum | — | — | 5 | — | — |
| DHEA | 3 | 1 | 5 | 2 | 1 |
| phosphatidylcholine | 7 | 250 | 20 | 6 | 4 |
| cetyl alcohol | — | 10 | 3 | — | — |
| C8–C10 triglyceride | — | 10 | — | — | — |
| isopropyl myristate | — | — | 7 | — | — |
| lanolin | — | — | 20 | 3 | — |
| stearic acid | — | — | — | 4 | 18 |
| glyceryl monostearate | — | — | — | 9 | — |
| olive oil | — | — | — | 8 | — |
| alpha-tocopherol milligrams | 10 | 20 | 5 | 5 | 5 |
| water-soluble: | | | | | |
| borax | 1 | — | — | — | — |
| water | 38 | 60 | — | 62 | 75 |
| ethanol | — | 60 | — | — | — |
| sorbitol | — | — | — | 5 | — |
| triethanolamine | — | — | — | 1 | — |
| glycerine | — | — | — | — | 6.5 |

-continued

| Example | 4 | 5 | 6 | 7 | 8 |
|---|---|---|---|---|---|
| potassium carbonate | — | — | — | — | 0.25 |
| methyl paraben preservative milligrams | 100 | 200 | 50 | 50 | 50 |
| TOTAL grams | 200 | 391 | 100 | 100 | 109.75 |

The results of these preparations are stable, non-separating creams in accordance with this invention.

EXAMPLES 9–13

Preparation of Lotions Containing Dehydroepiandrosterone and Phosphatidylcholine The following lotions are prepared by triturating the water-insoluble ingredients with a portion of the pre-mixed water-soluble ingredients to a smooth paste, and adding the remainder of the water-soluble ingredients with high speed stirring.

| Example | 9 | 10 | 11 | 12 | 13 |
|---|---|---|---|---|---|
| water-insoluble: | | | | | |
| Example 2 product | — | — | 10 | — | — |
| mineral oil | 45 | — | — | — | — |
| DHEA | 1 | 1.5 | — | 1.5 | 3 |
| phosphatidylcholine | 4 | 5 | — | 3.5 | 7 |
| cetyl alcohol | 1 | — | — | — | 4.2 |
| oleyl alcohol | — | — | — | 5 | — |
| C8–C10 triglyceride | — | — | — | 5 | — |
| lanolin | 1 | | | | |
| stearic acid | — | — | — | 5 | — |
| polyethylene glycol 200 monostearate | — | 15 | — | 9 | 2.8 |
| Polysorbate 80 | — | 1 | — | — | — |
| Magnesium aluminum silicate | — | 2.5 | — | — | — |
| water-soluble: | | | | | |
| sodium lauryl sulfate | 2 | — | — | — | — |
| water | 48 | 75* | — | 70* | 75.5* |
| triethanolamine | — | — | — | 1 | — |
| glycerine | — | — | 32 | 5 | 2 |
| carboxymethylcellulose sodium | — | — | 2 | — | — |
| ammonium chloride | — | — | — | — | 0.5 |
| TOTAL | 100 | 100* | 44 | 100* | 100* |

*Includes 0.1–0.2 g methyl p-hydroxybenzoate preservative

The results of these preparations are lotions in accordance with this invention that are readily redispersed by shaking if they should separate on standing.

EXAMPLES 14–15

Preparation of Gels Containing Dehydroepiandrosterone and Phosphatidylcholine The following gels are prepared by warming together the ingredients shown with stirring, and cooling to ambient with continued mild agitation.

| Example | 14 | 15 |
|---|---|---|
| water-insoluble: | | |
| Example 2 product | — | 10 |
| DHEA | 2 | — |
| phosphatidylcholine | 4 | — |
| polyacrylic acid | 1.2 | — |
| glyceryl monostearate | 5 | — |
| water-soluble: | | |
| ethyl alcohol | 40 | 34 |
| water | 46.3 | 51.2 |
| triethanolamine | 1.5 | — |
| gelatin | — | 1.2 |
| pectin | — | 2.1 |
| agar | — | 1.5 |
| TOTAL | 100 | 100 |

The results of these preparations are thixotropic gels in accordance with this invention.

EXAMPLE 16

Transdermal Administration of a Composition Containing Dehydroepiandrosterone and Phosphatidylcholine BJR, a 46 year old postmenopausal woman had a long history of fatigue, anxiety, decreased libido, cellulite, and was mildly overweight and otherwise in apparent good health. She volunteered to test the effects of topical lecithin-DHEA. A fasting blood sample was drawn on day 1 through day 21 for complete blood count, chemistry panel and dehydroepiandrosterone sulfate serum levels.

She was given the following instructions.

1) Apply 30 ml (one tablespoon) of the cream to each thigh and rub it in well every morning for three weeks.

2) Wait for at least two hours before washing off the unabsorbed material on the skin.

The cream provided to her had the following composition:

| | |
|---|---|
| Phosphatidylcholine | 250 ml |
| Ethanol | 75 ml |
| Cetyl alcohol | 10 ml |
| Distilled water | 60 ml |
| Medium chain triglycerides | 10 ml |
| DHEA | 1000 mg |

BJR returned every third day for analysis.

Over three weeks she related a progressive sense of well being, increased energy and libido, and diminished anxiety. Objectively there was a three pound weight loss and somewhat less cellulite.

Baseline level of DHEA sulfate was 1.8 micrograms/ml. After 10 days and thereafter the serum DHEA sulfate level was over 4 micrograms/ml. There was no change in her complete blood count or liver function tests. There was also no staining or discoloration of her skin or clothing at any time during or after administering the composition.

The results of this example provide positive evidence of successful transdermal administration of DHEA to a person in accordance with this invention.

EXAMPLE 17

Transdermal Administration of a Composition Containing Dehydroepiandrosterone and Phosphatidylcholine and Attempted Transdermal Administration of Dehydroepiandrosterone without Phosphatidylcholine RRR, a 69 year old postmenopausal woman in apparent good health volunteered to try four different topical creams for two weeks at a time. Serum levels of DHEA were taken after seven and fourteen days.

1) Topical DHEA in cold cream (30 ml on two sites daily for two weeks) produced no change in serum DHEA levels.

2) Topical DHEA in aromatic carbocyclic permeation enhancer 10% concentration of DHEA in 30 ml on two sites daily for two weeks produced no change in serum DHEA levels.

3) Topical DHEA in aliphatic carbocyclic permeation enhancer with 10% concentration of DHEA in 30 ml on two sites daily for two weeks produced no change in serum DHEA levels.

4) Topical DHEA-phospholipid 10% concentration of DHEA in 30 ml on two sites daily produced a doubling of the baseline serum concentration by the 14th day.

The results of this example provide evidence of the unexpected advantage of phospholipid used together with DHEA to effect dramatically increased serum levels of DHEA.

EXAMPLE 18

Transdermal Administration of Dehydroepiandrosterone and Phospholipid on the Scalp GM, a 41 year old man volunteered to try DHEA-phospholipid in a lotion comprising 10% DHEA in phospholipid (without cetyl alcohol), 20 ml of glycerin, and two grams of carboxymethylcellulose. He was instructed to 1) shake the bottle of lotion well before each use, 2) for external use only, 3) apply 45 ml to the scalp nightly with a gauze pad and 4) wash out every morning.

After three months, GM experienced significant observable new hair growth as well as thickening of his existing hair.

The results of this example provide evidence of hair growth following transdermal administration of the composition of this invention.

EXAMPLE 19

Transdermal Administration of Dehydroepiandrosterone and Phospholipid on the Face DC, a 52 year old woman, volunteered to apply DHEA gel to one side of her face nightly for three months. 10% DHEA-phospholipid complex with gelatin, pectin, and agar was applied around the eye, mouth and forehead of the left side of the face.

After three months, there was a significant reduction of the number, width, and depth of the wrinkles on the left side of her face as compared to the right side.

The results of this example provide evidence of reduction of wrinkles following transdermal administration of the composition of this invention.

EXAMPLE 20

Transdermal Administration of Dehydroepiandrosterone and Phospholipid on the Hands AH, a 62 year old woman volunteered to apply DHEA-phospholipid hand cream daily for three months. Lonaolin and glyceryl monostearate were mixed with 5% DHEA-phospholipid complex.

AH was noted to have progressive younger looking hands, with less wrinkles, smoother skin, and less roughness.

The results of this example provide further evidence of reduction of wrinkles following transdermal administration of the composition of this invention.

EXAMPLE 21

Transdermal Administration of Dehydroepiandrosterone and Phospholipid by a Patch AM, a 62 year old man volunteered to try a dermal patch for three weeks. The patch had a central drug delivery reservoir surrounded by a peripheral adhesive area and a microporous membrane. A fresh patch was applied daily to any covered area of the body for three weeks. Serum levels of DHEA sulfate tripled by the end of the third week.

The results of this example provide further evidence of successful transdermal administration of DHEA to a person in accordance with this invention.

EXAMPLE 22

Measurement of Free DHEA in a Human Subject After Administration of DHEA

BLW, a 49 year old woman volunteered to have her plasma levels of free DHEA checked every 10 minutes after oral ingestion of 200 milligrams of DHEA. There was no appreciable rise in free DHEA levels as measured over 4 hours. However, there was a mild increase of DHEA-S level at 4 hours.

The following week BLW volunteered to have her plasma levels of free DHEA checked every 10 minutes after transdermal patch application of DHEA-phospholipid composition. At twenty minutes and thereafter, there was a two to four fold sustained increase of free DHEA plasma levels that was maintained for four hours. There was a mild increase of DHEA-S level at 4 hours only.

These results demonstrate the unexpected ability of the composition of this invention to sustainably enhance the plasma level of free DHEA as well as DHEA sulfate.

EXAMPLE 23

Treatment of Systemic Lupus Erythematosus with Dehydroepiandrosterone and Phospholipid ZB, a 42 year old woman with systemic lupus erythematosus (SLE) according to the AMERICAN COLLEGE OF RHEUMATOLOGY criteria consented to a clinical trial of topical DHEA. Topical cream containing DHEA and phosphatidylcholine was used on a daily basis to achieve double serum DHEA levels for 3 months.

Patient's and physician's overall assessment of disease activity improved. SLE Disease Activity Index score improved.

The results of this trial show the effectiveness of a composition of this invention in the treatment of systemic lupus erythematosus.

EXAMPLE 24

Treatment of Seropositive Rheumatoid Arthritis with Dehydroepiandrosterone and Phospholipid NP, a 52 year old woman with seropositive rheumatoid arthritis according to the American Colelge of Rheumatology criteria consented to a clinical trial of topical DHEA. Topical cream containing DHEA and phosphatidylcholine was used on a daily basis to achieve double or triple serum DHEA levels for 3 months.

Patient's and physician's overall assessment of disease activity improved.

The results of this trial show the effectiveness of a composition of this invention in the treatment of seropositive rheumatoid arthritis.

EXAMPLE 25

Treatment of Erectile Dysfunction with Dehydroepiandrosterone and Phospholipid

GS, a 43 year old man with erectile dysfunction consented to a clinical trial of topical DHEA. Topical cream containing DHEA and phosphatidylcholine was used on a daily basis to achieve double or triple serum DHEA levels for one month.

Patient's and physician's assessment of the patient's erectile dysfunction revealed modest improvement.

The results of this trial show the effectiveness of a composition of this invention in the treatment of erectile dysfunction.

The foregoing description is intended as illustrative and is not to be taken as limiting. Still other variations within the spirit and scope of this invention as defined by the claims are possible and will readily present themselves to those skilled in the art.

What is claimed is:

1. A non-staining topical composition in the form of a solution cream, lotion or gel for enhancing the serum concentration of dehydroepiandrosterone in a person being topically administered said composition, comprising an effective amount in the range of 0.1 grams to 25 grams per 100 grams of composition of at least one dehydroepiandrosterone compound selected from the group consisting of dehydroepiandrosterone and a fluorinated dehydroepiandrosterone and an amount effective to increase the transdermal transmission thereof in the range of 1 grams to 90 grams per 100 grams of composition of at least one phospholipid.

2. A composition according to claim 1 for at least doubling the baseline serum concentration of dehydroepiandrosterone in a person within ten days of topical administration of said composition to said person.

3. A composition according to claim 1 for achieving an above baseline serum concentration of dehydroepiandrosterone sustained for at least fourteen days.

4. A composition according to claim 1 for maintaining the plasma concentration of free dehydroepiandrosterone for at least four hours longer than by oral ingestion or by the normal human physiological secretion of the adrenal gland.

5. A composition according to claim 1 in which the dehydroepiandrosterone compound is dehydroepiandrosterone.

6. A composition according to claim 1 in which the dehydroepiandrosterone compound is a fluorinated dehydroepiandrosterone.

7. A composition according to claim 1 in which the phospholipid is phosphatidylcholine.

8. A composition according to claim 1 in which the phospholipid is phosphatidylethanolamine.

9. A composition according to claim 1 in which the phospholipid is phosphatidylserine.

10. A composition according to claim 7 in which the phospholipid is soy lecithin.

11. A composition according to claim 1 additionally including at least one topically acceptable carrier selected from the group consisting of medium chain triglycerides having six to ten carbon atoms in each fatty acid chain, straight chain aliphatic alcohols having twelve to twenty carbon atoms, ethanol, and water.

12. A composition according to claim 11 which is a solution including a concentration of dehydroepiandrosterone compound in the range of 0.5 to 15 grams per 100 grams of composition, a concentration of phospholipid in the range of 5 to 75 grams per 100 grams of composition, a concentration of volatile carrier in the range of 0 to 90 grams per 100 grams of composition, and a concentration of non-Volatile carrier in the range of 0 to 30 grams per 100 grams of composition.

13. A composition according to claim 1 which is a cream including a concentration of dehydroepiandrosterone compound in the range of 2 to 75 grams per 100 grams of composition, a concentration of emollient in the range of 0 to 50 grams per 100 grams, and a concentration of emulsifier in the range of 0 to 30 grams per 100 grams.

14. A composition according to claim 1 which is a lotion including a concentration of dehydroepiandrosterone compound in the range of 0.2 to 10 grams per 100 grams of composition, a concentration of phospholipid in the range of 2 to 30 grams per 100 grams of composition, a concentration of finely divided solid in the range of 0 to 5 grams per 100 grams of composition, and a concentration of non-volatile carrier in the range of 0 to 5 grams per 100 grams of composition.

15. A composition according to claim 1 which is a gel including a concentration of dehydroepiandrosterone compound in the range of 0.1 to 10 grams per 100 grams of composition, a concentration of phospholipid in the range of 2 to 50 grams per 100 grams of composition, a concentration of phospholipid in the range of 2 to 50 grams per 100 grams of composition, a concentration of finely divided solid in the range of 0 to 15 grams per 100 grams of composition, and a concentration of thickener in the range of 0 to 15 grams per 100 grams of composition, provided that the combined concentration of finely divided solid and thickener is at least 1 gram per 100 grams of composition.

16. A stable liquid concentrate suitable for preparing a composition according to claim 1, comprising 10 to 15 parts by weight of dehydroepiandrosterone, 50 to 80 parts by weight of phospholipid, 10 to 100 parts by weight of ethanol, 2 to 20 parts by weight of medium chain length triglyceride, and 1 to 10 parts by weight of cetyl alcohol.

\* \* \* \* \*